US00PP28579P2

(12) United States Plant Patent
Nishita et al.

(10) Patent No.: US PP28,579 P2
(45) Date of Patent: Oct. 24, 2017

(54) ***PORTULACA* PLANT NAMED 'SAKPOR012'**

(50) Latin Name: *Portulaca oleracea*
Varietal Denomination: SAKPOR012

(71) Applicant: Sakata Seed Corporation, Yokohama (JP)

(72) Inventors: Koichi Nishita, Shizuoka prefecture (JP); Michiyoshi Fuyama, Shizuoka prefecture (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,126

(22) Filed: Mar. 31, 2016

(51) Int. Cl.
*A01H 5/02* (2006.01)

(52) U.S. Cl.
USPC ..... Plt./471

(58) Field of Classification Search
USPC ..... Plt./471
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A *portulaca* plant particularly distinguished by having yellow flowers, long flower blooming period and a dense, compact, and mounding plant growth habit, is disclosed.

2 Drawing Sheets

Genus and species: *Portulaca oleracea.*
Variety denomination: 'SAKPOR012'.

BACKGROUND OF THE NEW PLANT

The present invention comprises a new and distinct variety of *portulaca* plant, botanically known as *Portulaca oleracea*, and referred to by the variety name 'SAKPOR012'.

'SAKPOR012' originated from a hybridization made in October 2007 in Kakegawa, Japan. The female parent was an unpatented proprietary *Portulaca* breeding line named 'Mo04-21A-2A' which had a yellow flower color and a domed plant growth habit. The male parent was an unpatented proprietary *Portulaca* breeding line named '6Bu-21-V4', characterized by its scarlet flower color and semi-mounding upright plant growth habit.

In October 2007, 'Mo04-21A-2A' and '6Bu-21-V4' were crossed and some $F_1$ seeds were obtained. In May 2008, the $F_1$ seed was sown in the greenhouse, and cultivated. In August 2008, four plants were selected from the $F_1$ group. In October 2008, F2 seeds were harvested after crossing within the four plants. The plants were evaluated, and plant line 'K2012-179' was selected for its yellow flower color, long flower blooming period and domed plant growth habit.

In March 2010, line 'K2012-179' was vegetatively propagated and cultivated. In August 2010, the breeder confirmed that line 'K2012-179' was fixed and stable. The line 'K2012-179' was propagated and cultivated again from 2011 to 2014 to reconfirm the lines' stability. The line was subsequently named 'SAKPOR012' and its unique characteristics were found to reproduce true to type in successive generations of asexual propagation.

SUMMARY

The following are the most outstanding and distinguishing characteristics of this new variety when grown under normal horticultural practices in Salinas, Calif.

1. Yellow flower color;
2. Long flower blooming period; and
3. A dense, compact, and mounding plant growth habit.

CROSS REFERENCE TO RELATED APPLICATIONS

Plant Breeder's Rights for 'SAKPOR012' were applied for in Japan on Sep. 9, 2014 (Application number 29525). 'SAKPOR012' has not been made publicly available or sold more than one year prior to the filing date of this application.

DESCRIPTION OF THE PHOTOGRAPHS

This *portulaca* plant is illustrated by the accompanying photographs which show the plant's overall plant habit including form, foliage, and flowers. The photographs are of a three month old plant grown in Salinas, Calif. under greenhouse conditions. The colors shown are as true as can be reasonably obtained by conventional photographic procedures.

DESCRIPTION OF THE NEW VARIETY

Figure 1:
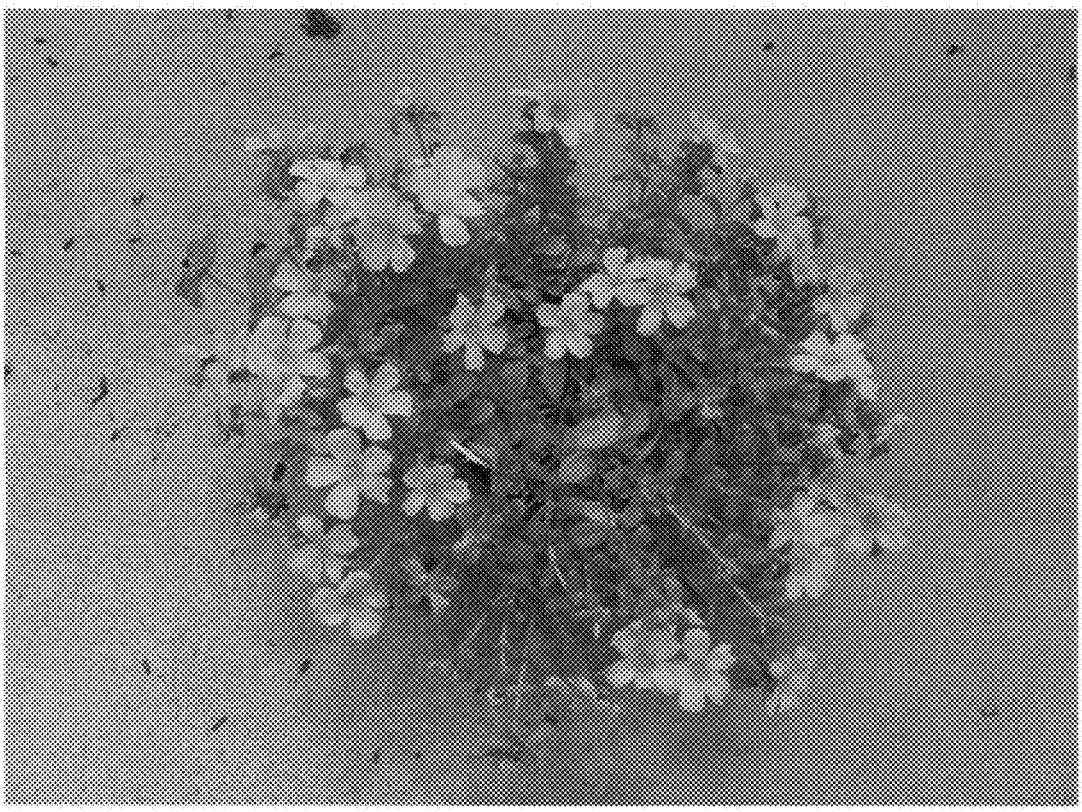
FIG. 1 shows the overall plant habit of the plant grown in a pot.
Figure 2:
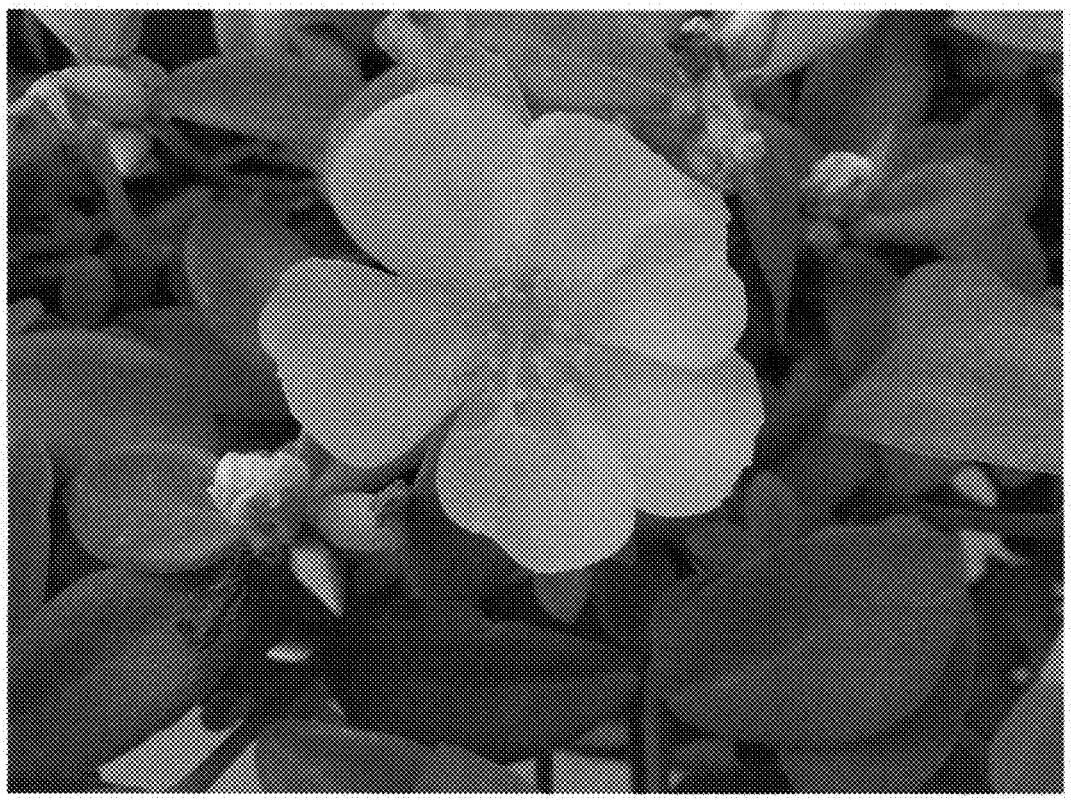
FIG. 2 shows a close-up of the mature inflorescence of the plant.

The following detailed descriptions set forth the distinctive characteristics of 'SAKPOR012'. The data which define these characteristics were collected from three month old plants grown in Salinas, Calif. Color references are to The R.H.S. Colour Chart of The Royal Horticultural Society of London (R.H.S.), 4$^{th}$ edition (2001).

Classification:

*Family.*—Portulacaceae.
*Botanical.*—*Portulaca oleracea.*
*Common.*—Purslane.
*Designation.*—'SAKPOR012'.

Parentage:
*Female parent.*—'Mo04-21A-2A' (unpatented).
*Male parent.*—'6Bu-21-V4' (unpatented).
Growth:
*Time to produce a rooted cutting.*—About 2 weeks.
*Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.
Plant description:
*Habit and form.*—Dense, compact, and mounding.
*Height.*—Approximately 8.0 cm from soil line to top of foliage.
*Spread.*—Approximately 34.0 cm.
*Time and conditions to produce a rooted cutting.*—2 weeks.
*Life cycle.*—Annual.
*Flowering requirements.*—Blooms repeatedly from spring to fall.
Stems:
*General description.*—Round with lateral ridges.
*Stem color.*—Closest to RHS 182C (Greyed-Red) with very slight RHS 145C (Yellow-Green).
*Anthocyanin color.*—RHS 59A (Red-Purple).
*Pubescence.*—Absent.
*Stem diameter.*—2.0 mm to 3.0 mm.
*Stem length.*—11.0 cm to 16.0 cm.
*Internode length.*—1.0 cm to 1.5 cm.
*Branching.*—Abundant.
Leaves:
*Arrangement.*—Alternate.
*Shape.*—Oblanceolate.
*Apex.*—Acute.
*Base.*—Rounded.
*Margin.*—Entire.
*Leaf attachment.*—Petiolate.
*Surface appearance (both surfaces).*—Dull, slightly waxy.
*Leaf length.*—2.0 cm.
*Leaf width.*—1.1 cm.
*Leaf thickness.*—Less than 1.0 mm.
*Surface texture (both surfaces).*—Dull, slightly waxy, soft.
*Leaf color.*—Upper surface: Closest to but brighter than RHS 146A (Yellow-Green) with most leaves having RHS 59B (Red-Purple) at edge. Lower surface: RHS 148B (Yellow-Green) with most leaves having RHS 59B (Red-Purple) at edge.
*Leaf surface pubescence.*—Absent.
*Venation.*—Only the mid vein is visible.
*Petiole.*—Absent.
*Fragrance.*—Absent.
Inflorescence:
*Inflorescence type.*—Solitary, sessile.
*Flowering habit.*—Determinate.
*Time to bloom from propagation.*—6 to 8 weeks.
*Lastingness of individual blooms on the plant.*—1 day.
*Flower diameter.*—3.0 cm.
*Flower depth.*—0.5 cm to 1.0 cm.
*Fragrance.*—Absent.
Flower bud:
*Surface appearance and texture.*—Shiny, pubescent.
*Shape.*—Lanceolate.
*Bud length.*—8.0 mm.
*Bud diameter.*—3.0 mm.
*Bud color.*—RHS 145A (Yellow-Green) with closest to RHS 13C (Yellow).
Corolla:
*Shape.*—Five distinct petals, free, petals are heart-shaped with a square base.
*Petal pubescence.*—Glabrous.
*Petal size.*—Length: 1.6 cm. Width: 1.2 cm.
*Petal apex.*—Retuse.
*Petal margin.*—Double lobed.
*Petal color.*—Upper surface: RHS 12A (Yellow). Lower surface: Closest to RHS 12C (Yellow).
Calyx:
*Arrangement.*—Composed of two sepals, free.
*Sepals.*—Shape: Elliptic. Apex: Cuspidate. Margin: Entire, slightly sinuate. Sepal length: 6.0 mm. Sepal diameter: 5.0 mm. Sepal color: Closest to RHS 144B (Yellow-Green) and translucent. Texture (both surfaces): Soft, dull and slightly sticky. Appearance: Double lobed, slightly sinuate.
Reproductive organs: Androecium.
*Stamen number.*—Many.
*Stamen form.*—Free.
*Stamens color.*—Anther: RHS 21B (Yellow-Orange). Filament color: RHS 14B (Yellow-Orange).
*Stamen length.*—5.0 mm.
*Pollen amount.*—Minimal.
*Pollen color.*—RHS 21B (Yellow-Orange).
*Fragrance.*—Absent.
*Placental arrangement.*—Central.
*Pistil number.*—1 (per inflorescence).
*Pistil length.*—1.1 cm.
*Stigma color.*—RHS 7A (Yellow).
*Stigma length.*—3.0 mm.
*Style length.*—7.0 mm.
*Style color.*—RHS 7A (Yellow).
*Seed production.*—Absent.
Disease and insect resistance: None observed.
Environmental conditions, disease and insect resistance: None observed.

COMPARISON WITH PARENTAL LINES AND KNOWN VARIETY

'SAKPOR012' is a distinct variety of *Portulaca* owing to its yellow flower color and domed plant habit. 'SAKPOR012' is distinguished from its parents as shown below in Table 1.

TABLE 1

| Comparison with Parental Lines | | | |
|---|---|---|---|
| Characteristic | 'SAKPOR012' | Female parent: 'Mo04-21A-2A' | Male parent: '6Bu-21-V4' |
| Flower color | Yellow | Lighter yellow than 'SAKPOR012' | Scarlet |
| Plant growth habit | Domed | Domed | Semi-mounding, Upright |

'SAKPOR012' is most similar to the variety SUN DANCE 'Lemon Yellow', also known as 'SAKPOR005' (U.S. Plant Pat. No. 24,599) however, there are differences in flower petal color and plant growth habit as described in the table below.

TABLE 2

| Comparison with Similar Variety | | |
|---|---|---|
| Characteristic | 'SAKPOR012' | SUN DANCE 'Lemon Yellow' |
| Flower petal color, upper surface | RHS 12A (Yellow) | RHS 8A (Yellow) |
| Plant growth habit | Domed | Semi-mounding, upright |

We claim:

1. A new and distinct variety of *portulaca* plant named 'SAKPOR012' as illustrated and described herein.

* * * * *